| United States Patent [19] | | [11] | 4,089,804 |
|---|---|---|---|
| Falk | | [45] | May 16, 1978 |

[54] METHOD OF IMPROVING FLUORINATED SURFACTANTS

[75] Inventor: Robert A. Falk, New City, N.Y.

[73] Assignee: Ciba-Geigy Corporation, Ardsley, N.Y.

[21] Appl. No.: 756,031

[22] Filed: Dec. 30, 1976

[51] Int. Cl.$^2$ ............................................. B01F 17/16
[52] U.S. Cl. .................................... 252/355; 252/351; 252/356; 252/357
[58] Field of Search ................ 252/351, 353, 355–357

[56] References Cited

U.S. PATENT DOCUMENTS

| 2,759,019 | 8/1956 | Brown et al. | 252/355 X |
|---|---|---|---|
| 2,764,603 | 9/1956 | Ahlbrecht | 252/357 X |
| 2,915,554 | 12/1959 | Ahlbrecht et al. | 252/355 X |
| 3,734,962 | 5/1973 | Niederprüm et al. | 252/355 X |
| 3,759,981 | 9/1973 | Hager et al. | 252/356 X |
| 3,772,195 | 11/1973 | Francen | 252/355 X |
| 3,836,552 | 9/1974 | Stach et al. | 252/357 X |

*Primary Examiner*—Richard E. Schafer
*Assistant Examiner*—E. Suzanne Park
*Attorney, Agent, or Firm*—Edward McC. Roberts; Michael W. Glynn; Prabodh I. Almaula

[57] ABSTRACT

Surface properties of solutions of fluorinated surfactants are improved by employing a fluorinated synergist $(R_f)_n T_m Z$ wherein $R_f$ is a perfluorinated aliphatic group, T is alkylene, arylene, alkylenethio alkylene, alkyleneoxyalkylene or alkyleneiminoalkylene, Z is a neutral or a polar group, $n$ is 1 or 2 and $m$ is 0 to 2. The resulting synergistic surfactant compositions are useful for all applications where surfactants are employed.

8 Claims, No Drawings

METHOD OF IMPROVING FLUORINATED SURFACTANTS

BACKGROUND OF THE INVENTION

Numerous surfactant applications depend on the attainment of low surface tensions. Whereas conventional hydrocarbon surfactants can attain surface tensions of as low as 23 dynes/cm, fluorinated surfactants are unique in that they can attain surface tensions of 15–20 dynes/cm, and at best of 14.5 dynes/cm. Such extremely low surface tensions are, however, only reached at high concentrations of fluorinated surfactants and only with highly specific structures. Since fluorinated surfactants are exceedingly expensive, it is imperative that the lowest surface tension is attained with the minimum quantity of surfactants.

The problem of attaining the lowest possible surface tension with fluorinated surfactants has been the subject of innumerable patents and publications, which detail specific and idealized structures having such properties.

In all cases the preferred candidate surfactants have distinctive and highly specific structures, which if varied even slightly drastically alter the attainable surface tensions. A fundamental reason that the attainment of a minimal surface tension at the lowest practicable use level is not easily answered is that the surface tension decreases as the fluorinated tail increases, while the solubility generally decreases so markedly when even one —$CF_2$— group is added that precipitation of the sparingly soluble fluorosurfactant frequently occurs.

It has long been known that the surface tension of hydrocarbon surfactants, which at best is 26–27 dynes/cm, can be depressed to 23 dynes/cm with sparingly soluble alcohols. In fact, the adventitious nature of this effect is so marked that surface tension curves of conventional commercial surfactants frequently have minima unless the surfactant is scrupulously purified.

Bernett and Zisman, *J. Phys. Chem*, 65, 448 (1961), teach that synergistic mixtures of conventional hydrocarbon surfactants and fluorinated 1,1-dihydro alcohols can be prepared which attain low surface tensions with smaller concentrations of the fluorinated agent. The resultant solutions are, however, unstable and the fluorinated alcohols are, moreover, volatile and acidic. With the ammonium salt of a perfluoronoanoic acid, the fluorinated 1,1,-dihydroalcohols are not sufficiently soluble and eventually form gelatinous precipitates.

DETAILED DISCLOSURE

The instant invention is directed to a method of improving the surface tension property of cationic, anionic non-ionic amphoteric or mixed function fluorinated surfactants by incorporating therewith a fluorinated synergist of the formula $$(R_f)_n T_m Z$$

wherein $R_f$ is a straight or branced chain perfluoroalkyl of 1 to 18 carbon atoms or said perfluoroalkyl substituted by perfluoroalkoxy of 2 to 6 carbon atoms, $n$ is 1 or 2, T is $R_3$ or —$R_3SCH_2CHR_1$— where $R_3$ is straight or branched chain alkylene or haloalkylene of 1 to 12 carbons, arylene of 6 to 12 carbons, alkylenethioalkylene or alkyleneoxyalkylene or alkyleneiminoalkylene of 2 to 12 carbons wherein in said imino group the nitrogen atom is secondary or tertiary, and $R_1$ is hydrogen or alkyl of 1 to 12 carbons, Z is a neutral or a polar group selected from —$CONR_1R_2$, —CN, —$CONR_1COR_2$, $SO_2NR_1R_2$, —$R_3$-($O_2CR_1$) and —$CO_2R_1$ where $R_1$ and $R_2$ are independently hydrogen, alkyl of 1 to 12 carbons or alkyl of 1 to 12 carbons substituted with 1 or more —OH, —$COCH_3$, —SH, —$COHN(CH_3)$ and $R_3$ is as defined above, and $m$ is an integer from 0 to 2 and preferably 1.

The surface tension of cationic, anionic, non-ionic amphoteric or mixed function fluorinated surfactants is improved by the use of a fluorinated synergist regardless of the specific structure of the surfactant. For the purpose of illustration the fluorinated surfactants can be represented by the general formula $$(R_f)_n A_m Q$$

wherein $R_f$, $n$ and $m$ are as defined above and Q is a water solubilizing group which is an anionic, cationic, non-ionic or amphoteric moiety, or a combination of such moieties.

Typical anionic groups of Q are carboxylic, ammonium or metal carboxylate where the metal is an alkali or alkali earth metal, especially sodium, potassium, calcium, magnesium and the like, sulfinic or sulfonic acid group or ammonium or a metal salt thereof or phosphonic ($OP(OH)_2$) or phosphoric ($OP(OH)_3$ acid group or ammonium or metal salt thereof. Typical cationic groups of Q are —$NH_2$, —NHR where R is lower alkyl of 1 to 4 carbons, —$NR_3'X$ where $R^1$ is hydrogen or lower alkyl and X is an anion such as a halogen, especially chloride, sulfate, phosphate, hydroxyl etc. Typical non-ionic groups of Q are amine oxides and groups derived from polyethylene oxide and mixed polyethylene oxide- polypropylene oxide polyols. Typical amphoteric and mixed groups are respectively —$N^+(CH_3)_2C_2H_4CO_2^-$, —$N(CH_3)(C_2H_4CO_2H)\rightarrow O$ and the like. As to the mixed group surfactants it is meant those of fluorinated surfactants which within the same molecule contain anionic and cationic moieties or anionic and non-ionic moieties or cationic and non-ionic moieties or cationic and amphoteric moieties or anionic and amphoteric moieties or non-ionic an amphoteric moieties. The above mentioned classes of fluorinated surfactants are also exemplified in my copending application, Ser. No. 642,272, which disclosure is incorporated herein by reference.

The $R_f$ group can be, as stated above, broadly a perfluoroalkyl of 1 to 18 carbons, but preferably it is a perfluoroaliphatic of 5 to 12 carbon atoms.

The synergist component terminates in a covalently bonded group —$T_m Z$ which is not critical as such. However, the overall solubility property as determined by the interrelationship of the moieties $R_f$, T and Z are important in establishing the effectiveness of the synergist. It is generally necessary that the combination of the fluorinated radical and the terminating group be so balanced that the solubility of said synergist in water at 25° C. is minimal, generally below 0.01% by weight. In the case of $R_f$-surfactant/$R_f$-synergist compositions, the solubility of the composition should be at least 0.1% by weight and in order to function affectively as a useful composition should provide a surface tension below 28 dynes/cm, preferably below 23 dynes/cm in aqueous or aqueous/solvent solution.

A is a multivalent linking group, preferably a divalent group such as alkylene of 1 to 12 and preferably of 1 to 4 carbon atoms; arylene such as phenylene, alkyl substituted phenylene or the group $C_6H_5YC_6H_5$ where Y is alkylene of 1 to 4 and preferably methylene, oxygen or sulfur; sulfonamide alkylene, carbonamidoalkylene and the like. It should be noted that in some instances more than one $R_f$ group may be bonded to a single Q group and in other instances, a single $R_f$ group may be linked to more than one Q group, or any be linked by a single Q group to more than one polar solubilizing group.

The fluorinated synergistic compound generally has a very limited solubility in water, but an enhanced solubility in the presence of the fluorinated surfactant. The critical aspect of the invention is that diverse fluorinated surfactants can be used for purposes of the invention which do not have idealized surface active properties. The synergistic additive effectively permits the resultant compositions to have markedly superior surface properties.

Consequently, the major component of these compositions may be a fluorinated surfactant which is chosen not on the basis of unique surface properties but on the basis of its economic feasibility of synthetic availability. In fact, it may contain a mixture of fluorinated telomer derived end groups from $C_4F_9-$ to $C_{14}F_{29}-$, be derived from fluorinated surfactants with highly branched tails, which do not generally exhibit good surface properties, or may contain some degree of hydrogen or chlorine substitution.

Because the synergistic additive is neutral, it is compatible with anionic, cationic, non-ionic or amphoteric structures, all of which give compositions with improved properties. This permits the choice of a fluorochemical surfactant type for an application independent of its surface properties and more nearly based on its price and availability.

The fluorochemical synergists are generally inexpensive and are readily attainable fluorochemical derivatives. They too may contain a mixture of fluorinated telomer derived end groups from $C_4F_9-$ to $C_{14}F_{29}-$, but preferably the lower, more soluble homologs. While the synergists can have diverse functionalities, the most effective synergists are neutral yet contain highly polar functions and most preferably polar functions that can be solubilized by hydrogen bonding. Strongly acidic or basic, corrosive or volatile, or otherwise unstable fluorochemical derivatives are not recommended as synergists for purposes of this invention.

The resultant fluorinated synergist/fluorinated surfactant compositions described in this invention can be used advantageously in place of conventional fluorinated surfactants for all purposes for which said conventional fluorinated surfactants are recommended. Naturally, various synergist/surfactant mixtures will be preferable for special considerations. For example, while cationic or anionic surfactant derived compositions may exhibit special substantivity, amphoteric or non-ionic fluorosurfactants may be more preferable for compatibility with the overall formulation. Thermal or hydrolytic stability considerations may lead to the choice of particularly stable functionalities for both synergist and surfactant, e.g. acid plating baths; non-ionic surfactant derived compositions may have special utility in non-aqueous or low foaming formulations; cationic surfactant derived compositions may be particularly synergistic with disinfectants. These examples are merely exemplary of the synergistic compositions, and preferred compositions should be chosen with due regard to the actual application. These compositions, just as conventional fluorochemical surfactants, are useful to improve or impart properties such as wetting, penetration, spreading, leveling, foam stability, flow properties, emulsification, dispersion, and oil and water repellency. Based on these unique properties are numerous applications, some of which follow. Although applications are suggested for a particular use area, the general applicability of each concept is inferred for other applications.

PLASTICS AND RUBBER INDUSTRY

Emulsifying agent for polymerization, particularly fluoromonomers

As a latex stabilizer

To aid in the preparation of agglomerates of powdered fluorocarbon polymers

In synergistic mixtures with hydrocarbon surfactants to wet low energy surfaces including natural and synthetic rubbers, resins, plastics As an adjuvant for foam applications and as foaming agents to aid in leak detection As a foam additive to control spreading, crawling, edge buildup As a mold release agent for silicones, etc.

In refractory processes

As an antimist film former

Additive for elimination of trapped air in plastic laminates

Wetting agent for resin molds for definition, strength

Hot- melt additive for oil and grease repellency

Resin additive for improved wetting of and bonding with fillers

Flow modifier for extruding hot melts: spreading, uniformity, anticratering

Adjuvant for resin etchant

Mold release agent, demolding agent

Retarder for plasticizer migration or evaporation

Internal antistatic agent for polyolefins

Antiblocking agent for polyolefins

PETROLEUM INDUSTRY

Wetting assistant for oil well treatments, drilling muds

As a film evaporation inhibitor for gasoline, jet fuel, solvents, hydrocarbons

Lubricating, cutting oil improver, to improve penetration times

In extreme pressure EP lubricants

Oil spill collecting agent

Additive to improve tertiary oil well recovery

TEXTILE AND LEATHER INDUSTRIES

Soil release and soil proofing agent

Oil/water repellent textile and leather treatment

Wetting agent to improve coverage and penetration of pores of substrates

Antifoaming agent in textile treatment baths

Wetting agent for finish-on-yarn uniformity

Penetrating agent for finishes on tow, heavy denier fibers

Emulsifying agent/lubricant for fiber finishes

Cleaner/metal treating agent for polymerization equipment

Flow modifier for spinning of hot melts, solutions

Additive for fabric finishes for spreading, uniformity

Wetting agent for dyeing

Penetration aid for bleaches
Wetting agent for binder in nonwoven fabrics

PAINT, PIGMENT AND FINISHING INDUSTRIES

Leveling, anticratering adjuvant for finishes and paints
Adjuvant for control of soiling
Agent to control differential evaporation of solvents
Leveling agent for floor waxes
Adjuvant for waxes to improve oil and water repellency
Adhesion improver for oily or greasy surfaces
To combat pigment flotation problems
Improver for automotive finishes, based on water-based coatings in which the pigments are rendered nonreactive
Pigment grinding aid to promote wetting, dispersion, color development
Foam generator substance for the application of dyes, inks
Electrolytic conversion coatings

MINING AND METAL WORKING INDUSTRIES

In cleaning agents for property improvement
Additive for solvent cleaning
Additive for metal pickling baths to increase life and acid runoff
Additive for chrome electroplating: surface tension reduction, foaming
Additive for soldering flux, especially for electronic circuitry
Protective agent for coatings (tarnish resistance, grease repellency)
Corrosion inhibitor
Additive for etchant solution for improved definition
To form antimist films and anticondensation surfaces
Plastic preplate and silicon etchant technology
In soldering flux for microelectronics to reduce foaming
In chemical roughing agent solutions, prior to galvanization
As a colloidal dispersion aid for magnetic solids
Protective coatings for aluminum and as an antiblocking agent
Wetting agent for leaching copper ores and as a froth flotation agent
To promote ore wetting and quicker breaking of the protective oxide layer

PHARMACEUTICAL INDUSTRY

Improve the properties and penetration of antimicrobial agents
Improve the properties of biochemicals, biocides, algicides, bacteriocides and bacteriostats
Improve the strength, homogeneity, and reduce the permeability of encapsulated materials
Emulsify fluorochemical blood substitutes

AGRICULTURE AND FORESTRY

Wetting agent for herbicides, fungicides, weed killers, hormone growth regulators, parasiticides, insecticides, germicides, bactericides, nematocides, microbiocides, defolients and fertilizers
As an ingredient in chemosterilents, insect repellants and toxicants
For wettable powder pesticides and chemical powders
Corrosion inhibitor for chemical applicators
Wetting agent for foliage
Wetting additive for live stock dips, or to wet sheep skins during desalination
Wetting adjuvant for manufacture of plywood veneer
Penetrant for preservative impregnation
Pulping aid
For cleaning tubes in paper making, dyeing
Grease/oil repellents for paper

FIRE FIGHTING

Wetting agent for fighting forest fires
Ingredient of AFFF, aqueous film forming extinguishing agents
Component of fluoroprotein foams
Additives to dry chemical extinguishing agents
Agent in aerosol-type extinguishers
Wetting agent for sprinkler water

AUTOMOTIVE, BUILDING MAINTENANCE AND CLEANING

Wetting agent for cleaning compositions
Additive for alkaline cleaners
Glass cleaner
Wetting agent for automobile waxes
Adjuvant to improve oil/water repellency of wax
Lubricant/corrosion inhibitor for antifreeze
Rinse-aid for car washes
In dry cleaning compositions and solvent cleaners, for water displacement and foaming. May improve soil suspension and decrease redeposition
Foaming agents for pipe cleaning
Anti-mist film foamer for glass and plastics
In foams for dust suppresion
Cleaner for building exteriors
For acidic concrete cleaners
Air entrainment additive for low density concrete
Bubble foamer for air tracing, in ventilating systems

HOUSEHOLD, COSMETIC AND PERSONAL PRODUCTS

Rinse-aid for dishwashing
Liquid polishing compositions
Floor polish leveling agent
Additive for alkaline oven cleaners
Synergistic improver for disinfectants
Carpet cleaners
Synergistic wetting agent in detergent formulations
Additive for protective coatings on metals (tarnish resistance, grease resistance)
Gloss and antistatic improver
Hair shampoo ingredient
Shaving foam ingredient
Oil and water repellent cosmetic powders ingredient
Ingredient of lotions or creams for skin or hair
Ingredient of skin protection creams

PHOTOGRAPHY AND GRAPHIC ARTS

Printing ink additive for ink flow and leveling, both aqueous and solvent based.
Wetting agent for writing inks
To combat pigment flooding and flotation in printing inks
To form ink repellent surfaces for waterless lithoplates, or electrographic coatings.
Prevent reticulation of gelatin layers and improve uniformity
Assist in film drying Improve film coatings and reduce "contraction flecks"
  Wetting, leveling, anti-cratering assist agent
  Surfactant for developer solutions
  Photoemulsion stabilizer
  Prevent photo-lubricant agglomeration
  Coating aid in the preparation of multiple layer film elements
  Antistatic wetting agent for film coatings
  Antifogging agent for films
  Bonding agent for fillers and fluoropolymer films
  In coatings for nematic liquid crystal cells Illustrative examples of $R_f$-anionics which can be used in the compositions of this invention are the below shown acids and their alkali metal salts. Preferred anionic groups are carboxylate and sulfonate. The anionic surfactant should generally contain 30–65% of carbon bound fluorine in order to attain suitable solubility properties. The anionic surfactant may be present as free acid, an alkali metal salt thereof, ammonium, or substituted ammonium. The patent numbers appearing in parenthesis are patents which more fully disclose the represented class of compounds. The disclosures of these patents are incorporated herein by reference.

| Carboxylic Acids and Salts thereof | |
|---|---|
| $R_fCOOH$ | (Scholberg et al, J. Phys. Chem. 57,923-5(1953)) |
| $R_f(CH_2)_{1-20}COOH$ | (Ger. 1,916,669) |
| $R_fO(CF_2)_{2-20}COOH$ | (Ger. 2,132,164) |
| $R_fO(CF_2)_{2-20}(CH_2)_{2-20}COOH$ | (Ger. 2,132,164) |
| $R_fO(CH_2)_{1-20}COOH$ | (U.S. 3,409,647) |
| $R_fSO_2N(C_2H_4)CH_2COOH$ | (U.S. 3,258,423) |
| $R_fO(CF_2O)_3CF_2COOH$ | (Fr. 1,531,902) |
| $R_fO\left(\begin{array}{c}CF_2CFO\\|\\CF_3\end{array}\right)_3 CF_2COOH$ | |
| $R_fO[CF(CF_3)CF_2O]CF(CF_3)CON(CH_3)CH_2COOH$ | (U.S. 3,798,265) |
| $(C_2F_5)_2(CF_3)CCH_2COOH$ | (Brit. 1,176,493) |
| $C_{10}F_{19}OC_6H_4CON(CH_3)CH_2COOH$ | (Brit. 1,270,662) |
| $R_f(CH_2)_{1-3}SCH(COOH)CH_2COOH$ | (U.S. 3,706,787) |
| $R_f(CH_2)_{1-12}S(CH_2)_{1-17}COOH$ | Ger. 2,239,709; U.S. 3,172,910 |

| Sulfonic Acids and Salts Thereof | |
|---|---|
| $R_fSO_3H$ | (U.S. 3,475,333) |
| $R_fC_6H_4SO_3H$ | (Ger. 2,134,973) |
| $R_f(CH_2)_{1-20}SO_3H$ | (Ger. 2,309,365) |
| $R_fSO_2NHCH_2C_6H_4SO_3H$ | (Ger. 2,315,326) |
| $R_fSO_2N(CH_3)(C_2H_4O)_{1-20}SO_3H$ | (S.A. 693,583) |
| $R_fCH_2CH_2OCH_2CH_2CH_2SO_3H$ | (Can. 842,252) |
| $R_fOC_6H_4SO_3H$ | (Ger. 2,230,366) |
| $C_{12}F_{23}OC_6H_4SO_3H$ | (Ger. 2,240,263) |
| $(C_2F_5)_2CO(CH_2)_3SO_3H$ | (Brit. 1,153,854) |
| $CF_3(C_2F_5)_2CO(CH_2)_3SO_3H$ | (Brit. 1,153,854) |
| $(C_2F_5)_2(CF_3)CCH=C(CF_3)SO_3H$ | (Brit. 1,206,596) |
| $R_fOCF(CF_3)CF_2OCF(CF_3)CONHCH_2SO_3H$ | (U.S. 3,798,265) |
| $R_f(CH_2)_{1-0}O_2-(C_2H_4O)_{1-12}SO_3H$ | (Ger. 2,310,426) |

| Phosphonates, Phosphates, Related Phosphoro Derivatives, and Salts Thereof | |
|---|---|
| $R_fPO(OH)_2, (R_f)_2PO(OH)$ | (Ger. 2,110,767) |
| $R_fSO_2N(Et)C_2H_4OPO(OH)_2$ | (Ger. 2,125,836) |
| $R_fCH_2OPO(OH)_2$ | (Ger. 2,158,661) |
| $C_8F_{17}OC_6H_4CH_2PO(OH)_2$ | (Ger. 2,215,387) |
| $R_fOC_6H_4CH_2PO(OH)_2$ | (Ger. 2,230,366) |

| Others (and Salts Thereof) | |
|---|---|
| $R_fSO_2N(CH_3)C_2H_4OSO_3H$ | (Ger. 1,621,107) |

| Others (and Salts Thereof) | |
|---|---|
| $R_fC_6H_4OH$ | (U.S. 3,475,333) |
| $R_f(CH_2)_{1-20}S_2O_3Na$ | (Ger. 2,115,139) |
| $R_f(CH_2)_{1-20}SO_2N(CH_3)CH_2CH_2S_2O_3Na$ | (Ger. 2,115,139) |
| $R_f\ldots SO_2H$ | (U.S. 3,562,156) |

Illustrative examples of $R_f$-cationics and $R_f$-amphoterics which can be used in the compositions of this invention are described in Table 1a and 1b, but also include compounds more fully disclosed in the following patents and incorporated herein by reference.

| United States | | German | |
|---|---|---|---|
| 2,727,923 | 3,630,951 | 1,925,555 | 2,224,653 |
| 2,759,019 | 3,681,413 | 2,013,104 | 2,230,366 |
| 2,764,602 | 3,681,441 | 2,119,302 | 2,236,729 |
| 2,764,603 | 3,759,981 | 2,120,868 | 2,239,709 |
| 3,147,065 | 3,766,274 | 2,127,232 | 2,315,326 |
| 3,207,730 | 3,828,085 | 2,132,164 | 2,325,855 |
| 3,257,407 | 3,839,425 | 2,165,057 | 2,337,638 |
| 3,510,494 | 3,933,819 | 2,215,387 | 2,357,916 |
| | 3,941,705 | 2,219,642 | 2,438,868 |
| | 3,957,657 | | 2,523,402 |
| British | | French | Belgium |
| 1,270,662 | | 2,035,589 | 788,335 |
| 1,288,678 | | 2,128,028 | 801,585 |
| 1,289,436 | | | |

Illustrative examples of $R_f$-nonionics which can be used in the compositions of this invention are described in Table 1d, but also include compounds more fully disclosed in the following patents and incorporated herein by reference.

| United States | | German | | British |
|---|---|---|---|---|
| 2,723,999 | 1,925,555 | 2,215,388 | 2,325,855 | 1,130,822 |
| 3,621,059 | 1,966,708 | 2,230,366 | 2,334,346 | 1,148,486 |
| 3,721,700 | 2,160,852 | 2,244,028 | 2,337,638 | 1,155,607 |
| 3,883,596 | 2,215,386 | 2,250,718 | 2,501,239 | 1,176,492 |
| 3,952,075 | | | | |
| Belgium | | Netherlands | | Japanese |
| 817,369 | | 7,009,980 | | 75-157,275 |

Illustrative examples of $R_f$-synergists which can be used in the compositions of this invention are given in Table 2 and also include:

$C_8F_{17}SO_2NH_2$
$C_8F_{17}SO_2N(C_2H_5)CH_2CHOHCH_2OH$
$C_8F_{17}SO_2N(CH_3)CH_2CHOHCH_2OH$
$C_8F_{17}SO_2N(CH_2CH_2OH)_2$
$C_8F_{17}SO_2N(CH_2CH_2SH)_2$
$C_6F_{13}CH_2CH_2SCH_2CH_2CONHCH_2OH$
$C_8F_{17}SO_2N(CH_3)C_{10}H_{20}CH_2OH$
$C_7F_{15}CON(C_2H_5)CH_2CH_2OH$
$CF_3C_6F_{10}SO_2N(C_2H_5)CH_2CH_2OH$
$C_3F_7O(C_3F_6O)_2CF_2CON(CH_3)C_3H_6OH$
$C_8F_{17}SO_2N(C_4H_9)CH_2CHOHCH_2OH$

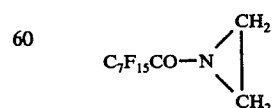

Also $(C_2F_5)_2(CF_3)C-CH_2CON(R)CH_2CH_2OH$ wherein R is H, $CH_3$, $C_2H_5$ or $CH_2CH_2OH$ disclosed in Brit. Pat. No. 1,395,751; $R_f(CH_2CFR_1)_mCH_2CH_2CN$ wherein $R_1 = H$ or $F$, $m = 1-3$ as disclosed in copending application U.S. Ser. No. 442,952, now abandoned, incorporated herein by reference; and compounds of the general structure: $R_f—CH_2CH_2—SO_xC_mH_{2m}A$ as described in Ger. Off. No. 2,344,889 wherein $x$ is 1 or 2, $R_f$ is as described above, $m$ is 1 to 3 and A is carboxylic ester, carboxamide or nitrile.

EXPERIMENTAL PART

Tables 1a through 1d list $R_f$-anionic, amphoteric, cationic, and nonionic surfactants and Table 2 lists $R_f$-synergists which are used in the examples following the tables.

The commercially available surfactants used in the examples are:

FC-95, which is an alkali metal salt of a perfluoroalkyl-sulfonic acid

FC-128, which is a perfluoroalkanesulfonamido alkylenemonocarboxylic acid salt as disclosed in U.S. Pat. No. 2,809,990.

FC-134, which is a cationic quaternary ammonium salt derived from a perfluoroalkanesulfonamidoalk- ylenedialkylamine as disclosed in U.S. Pat. No. 2,759,019, e.g.

$C_8F_{17}SO_2NHC_3H_6N(CH_3)_3I^-$

FC-430, which is a nonionic perfluoroalkanesulfonamido polyalkylene oxide derivative Zonyl FSA and FSP, anionics derived from linear perfluoroalkyl telomers Zonyl FSB, an amphoteric carboxylate derived from linear perfluoroalkyl telomers Zonyl FSC, a cationic quaternary ammonium salt derived from linear perfluoroalkyl telomers Zonyl FSN, a nonionic derived from linear perfluoroalkyl telomers Monflor 31 and 32, anionics derived from branched tetrafluoroethylene oligomers as disclosed in GB Pat. No. 1,148,486.

Monflor 72, a cationic derived from branched tetrafluoroethylene oligomers as disclosed in DT Pat. No. 2,224,653.

Monflor 52, a nonionic derived from branched tetrafluoroethylene oligomers as disclosed in Brit. Pat. No. 1,130,822, 1,176,492 and 1,155,607

Table 1a

Fluorinated Anionic Surfactants used in Examples 1 to 113

| $R_f$ Surfactant | Name | Formula | | | |
|---|---|---|---|---|---|
| A1 | 2-Methyl-2-(3-[1,1,2,2-tetra-hydroperfluoroalkylthio pro-pionamide)-1-propanesulfonic acid, sodium salt[1] | $R_fCH_2CH_2SCH_2CH_2CONHC(CH_3)_2CH_2SO_3Na$ wherein: | % $C_6F_{13}$ | % $C_8F_{17}$ | % $C_{10}F_{21}$ |
| | | | 39 | 41 | 13 |
| A2 | as above | | 44 | 42 | 10 |
| A3 | as above | | 52 | 35 | 8 |
| A4 | as above | | 60 | 36 | 4 |
| A5 | as above | | 32 | 42 | 21 |
| A6 | as above | | 27 | 44 | 23 |
| A7 | as above | | 20 | 48 | 26 |
| A8 | as above, 45% | | 100 | | |
| A9 | as above, 45% | | | 100 | |
| A10 | as above, 100% | | | | 100 |
| A11[2] | 1,1,2,2,-Tetrahydroperfluoro-alkylsulfonate, potassium salt | $R_fCH_2CH_2SO_3$ wherein: | 20 | 40 | 20 |
| A12[2] | Perfluoroalkanoic acid, potassium salt | $R_fCOOK$ | 32 | 62 | 6 |
| A13 | A8, magnesium salt | | 100 | | |
| A14 | FC-95[3a] | | | | |
| A15 | FC-128[3a] | | | | |
| A16 | Zonyl FSA[3b] | | | | |
| A17 | Zonyl FSP[3b] | | | | |
| A18 | Monflor 31[3c] | | | | |
| A19 | Monflor 32[3c] | | | | |
| A20 | | $C_8F_{17}SO_2N(C_2H_5)CH_2CO_2K$ | | | |
| A21 | | $C_8F_{17}SO_3K$ | | | |
| A22 | | $C_8F_{17}SO_2NHCH_2C_6H_4SO_3Na$ | | | |

[1]As disclosed in co-pending application Serial No. 642,270 Pat. No. 4,000,188, where $R_f$ is a mixture consisting principally of $C_6F_{13}$, $C_8F_{17}$, and $C_{10}F_{21}$ in the approximate ratio 2:2:1 or as stated. 35% solution in 17.5% hexylene glycol - 47.5% water or as otherwise stated.
[2]Approximate homolog distribution
[3]Commercial products of a) 3M, b) duPont, c) I.C.I.

Table 1b

Fluorinated Amphoteric Surfactants used in Examples 1 to 113

| $R_f$ Surfactant | Name or Formula | Formula | | |
|---|---|---|---|---|
| A23a[1,2] | N-[3-(dimethylamino)propyl]-2 and 3-(1,1,2,2-tetrahydroperfluoroalkylthio) succinamic acid, 60% solids | % $C_6F_{13}$ | % $C_8F_{17}$ | % $C_{10}F_{21}$ |
| | | 32 | 36 | 22 |
| A23b | " | 39 | 41 | 13 |
| A23c | " | 44 | 42 | 10 |
| A24 | $C_6F_{13}SO_2N(CH_2CO_2^-)C_3H_6\overset{+}{N}(CH_3)_3$ | | | |
| A25 | $C_6F_{13}CH_2CH_2SCH_2CH_2\overset{+}{N}(CH_3)_2CH_2CO_2^-$ | | | |
| A26 | $C_8F_{17}C_2H_4CONH(CH_2)_3\overset{+}{N}(CH_3)_2CH_2CH_2CO_2^-$ | | | |
| A27 | $C_6F_{13}SO_2N(C_3H_6SO_3^-)C_6H_6\overset{+}{N}(CH_3)_2(C_2H_4OH)$ | | | |
| A28 | $C_8F_{17}CH_2CH_2CH(CO_2^-)\overset{+}{N}(CH_3)_3$ | | | |
| A29 | $C_6F_{13}SO_2N(CH_2CH_2CO_2^-)C_3H_6\overset{+}{N}(CH_3)_2CH_2CH_2OH$ | | | |
| A30[3] | Zonyl FSB | | | |

Table 1b-continued
Fluorinated Amphoteric Surfactants used in Examples 1 to 113

| $R_f$-Surfactant | Name or Formula | Formula |
|---|---|---|
| A31 | $C_7F_{15}CONHC_3H_6\overset{+}{N}(CH_3)_2CH_2CH_2CO_2^-$ | |

[1] As disclosed in U.S. Serial No. 538,432
[2] Approximate homolog distribution
[3] Commercial product of duPont

Table 1c
Fluorinated Cationic Surfactants used in Examples 1 to 113

| $R_f$-Surfactant | Name or Formula |
|---|---|
| A32 | $C_8F_{17}SO_2NHC_3H_6\overset{+}{N}(CH_3)_3\bar{C}l$ |
| A33 | $C_8F_{17}SO_2NHC_3H_6\overset{+}{N}(CH_3)_2C_2H_5\bar{O}SO_2OC_2H_5$ |
| A34 | $C_8F_{17}SO_2NHC_3H_6\overset{+}{N}(CH_3)_3\bar{I}$ |
| A35 | $C_7F_{15}CONHC_3H_6\overset{+}{N}(CH_3)_3\bar{C}l$ |
| A36 | $C_8F_{17}SO_2NHC_3H_6\overset{+}{N}(CH_3)_2CH_2C_6H_5\bar{C}l$ |
| A37 | $C_8F_{17}SO_2N(CH_3)C_3H_6\overset{+}{N}(CH_3)_3\bar{I}$ |
| A38 |  |
| A39 | $C_6F_{13}CH_2CH_2SCH_2CH_2\overset{+}{N}(CH_3)_3\bar{I}$ |
| A40[1a] | FC-134 |
| A41[1b] | Zonyl FSC |
| A42[1c] | Monflor 71 |

[1] Commercial product of a) 3M, b) duPont, c) I.C.I.

Table 1d
Fluorinated Non-ionic Surfactants used in Examples

| $R_f$-Surfactant | Name or Formula |
|---|---|
| A43 | FC-430[1a] |
| A44 | Zonyl FSN[1b] |
| A45 | Monflor 52[1c] |

[1] Commercial products of
[a] 3M,
[b] duPont,
[c] I.C.I.

EXAMPLES 1 TO 17

Fluorinated surfactants of the diverse types as shown in Table 3 were compared at the same dilution in the presence of a typical $R_f$-synergist B6, with and without added magnesium sulfate. As is shown *without exception*, the observed surface tension is markedly reduced in the presence of $R_f$-synergist.

With magnesium sulfate alone (no synergist present) the anionic $R_f$-surfactants show a marked improvement in surface tension while the amphoterics, cationics and non-ionics show no appreciable change. This effect of a polyvalent metal ion on anionic $R_f$-surfactants is the subject of copending application.

When the $R_f$-synergist is used on the various surfactants in conjunction with magnesium sulfate not only are all the observed surface tensions markedly reduced, but the effect on $R_f$-anionic surfactants is especially pronounced.

The test solutions exhibit varying degrees of clarity and, significantly, many of the solutions are clear. It has been found that the addition of small quantities of conventional hydrocarbon surfactants to the cloudy compositions will frequently improve their compatibility.

Table 2
$R_f$-Synergists used in Examples

| $R_f$-Synergist | Name | Formula | | |
|---|---|---|---|---|
| | | $R_fCH_2CH_2SCH_2CH_2CONH_2$ wherein: | | |
| | | % $C_6F_{13}$ | % $C_8F_{17}$ | % $C_{10}F_{21}$ |
| B1 | 3-[1,1,2,2-tetrahydroperfluoroalkylthio]propionamide | 65 | 23 | 5 |
| B2 | as above | 67 | 10 | 1 |
| B3 | as above | 80 | 14 | 1 |
| B4 | as above | 71 | 23 | 2 |
| B5 | as above | 35 | 36 | 20 |
| B6 | as above | 100 | | |
| B7 | as above | | 100 | |
| | | $R_fCH_2CH_2SCH_2CH_2CN$ wherein: | | |
| B8 | 3-[1,1,2,2-tetrahydroperfluoroalkylthio]propionitrile | 10 | 42 | 12 |
| B9 | as above | 100 | | |
| B10 | as above | | 100 | |
| | | $R_fCH_2CH_2SCH_2CH(CH_3)CONH_2$ wherein: | | |
| B11 | 2-methyl-3-[1,1,2,2-tetrahydroperfluoroalkylthio]propionamide | 40 | 42 | 12 |
| B12 | as above | 100 | | |
| B13 | N-[2-(2-methyl-4-oxopentyl)]3-[1,1,2,2-tetrahydroperfluoroalkylthio propionamide] | $R_fCH_2CH_2SCH_2CH_2CONHC(CH_3)_2CH_2COCH_3$ wherein: | | |
| | | 40 | 42 | 12 |
| B14 | as above | 100 | | |
| B15 | N-methylol-3-[1,1,2,2,-tetrahydroperfluoroalkylthio]propionamide | 100 | | |
| B16 | perfluorooctanamide | 100 ($C_7F_{15}CONH_2$) | | |
| B17 | perfluorooctanonitrile | 100 ($C_7F_{15}CN$) | | |
| B18 | N-methyl-perfluorooctane sulfonamide | ($C_8F_{17}SO_2NHCH_3$) 100 | | |
| B19 | N-methyl, N-hydroxyethyl perfluorooctane sulfonamide | ($C_8F_{17}SO_2N(CH_3)CH_2CH_2OH$) 100 | | |
| B20 | 1,1,2,2-tetrahydroperfluoroalkylthioethylacetate | 100 ($R_fCH_2CH_2SCH_2CH_2OCOCH_3$) | | |
| B21 | 2-iodo,1,1,2,3,3 pentahydroperfluorononyl nitrile | $C_6F_{13}CH_2CHICH_2CN$ | | |

Table 3

Effect of R$_f$-Synergists on R$_f$-Surfactants

| | | |
|---|---|---|
| R$_f$-Surfactant | Variable | 1.67%[4] |
| R$_f$-Synergist | B6 | 0.33% |
| Solvent | | 25% |
| Magnesium Sulfate Heptahydrate | | 0.6% |

| Example Number | R$_f$-Surfactant | R$_f$-Synergist | MgSO$_4$ · 7 H$_2$O[2] | Surface Tension[1] | Clarity[1,3] |
|---|---|---|---|---|---|
| | none | + | − | 35 | c[5] |
| 1 | FC-95 | − | − | 26.0 | — |
| | FC-95 | + | − | 18.4 | a |
| | FC-95 anionic | − | + | 21.5 | — |
| | FC-95 | + | + | 15.7 | a |
| 2 | FC-128 | − | − | 20.4 | b |
| | FC-128 | + | − | 18.8 | c |
| | FC-128 anionic | − | + | 18.3 | c |
| | FC-128 | + | + | 17.1 | c |
| 3 | FC-134 | − | − | 18.5 | — |
| | FC-134 | + | − | 15.8 | — |
| | FC-134 cationic | − | + | 18.1 | — |
| | FC-134 | + | + | 15.8 | — |
| 4 | Monflor 31 | − | − | 26.0 | — |
| | Monflor 31 | + | − | 22.8 | b |
| | Monflor 31 anionic | − | + | 21.4 | a |
| | Monflor 31 | + | + | 20.0 | — |
| 5 | Monflor 52 | − | − | 22.7 | c |
| | Monflor 52 | + | − | 21.1 | c |
| | Monflor 52 non-ionic | − | + | 23.5 | c |
| | Monflor 52 | + | + | 21.8 | c |
| 6 | Monflor 71 | − | − | 28.5 | — |
| | Monflor 71 | + | − | 24.2 | — |
| | Monflor 71 cationic | − | + | 27.4 | — |
| | Monflor 71 | + | + | 22.9 | — |
| 7 | Zonyl FSA | − | − | 18.3 | — |
| | Zonyl FSA | + | − | 17.1 | a |
| | Zonyl FSA anionic | − | + | 17.9 | a |
| | Zonyl FSA | + | + | 16.9 | b |
| 8 | Zonyl FSP | − | − | 19.3 | — |
| | Zonyl FSP | + | − | 17.9 | b |
| | Zonyl FSP anionic | − | + | 18.8 | c |
| | Zonyl FSP | + | + | 17.9 | c |

[1] 6% dilution in distilled water; corresponds to 0.1% R$_f$-surfactant and 0.02% R$_f$-synergist
[2] Ingredient present (+), absent (−)
[3] Clarity: — = clear; a = opalescent; b = slight precipitate; c = precipitate
[4] Ingredients corrected for dilution as necessary; 100% actives
[5] Filtered solution for measurement of surface tension

| Example Number | R$_f$-Surfactant | R$_f$-Synergist | MgSO$_4$ · 7 H$_2$O[2] | Surface Tension[1] | Clarity[1,3] |
|---|---|---|---|---|---|
| 9 | Zonyl FSB | − | − | 17.8 | — |
| | Zonyl FSB | + | − | 16.3 | — |
| | Zonyl FSP amphoteric | − | + | 17.3 | — |
| | Zonyl FSB | + | + | 16.3 | — |
| 10 | Zonyl FSN | − | − | 20.8 | — |
| | Zonyl FSN | + | − | 18.1 | b |
| | Zonyl FSN non-ionic | − | + | 20.9 | — |
| | Zonyl FSN | + | + | 18.0 | a |
| 11 | Zonyl FSC | − | − | 19.9 | — |
| | Zonyl FSC | + | − | 15.6 | b |
| | Zonyl FSC cationic | − | + | 20.0 | — |
| | Zonyl FSC | + | + | 15.8 | — |
| 12 | A23b | − | − | 19.7 | — |
| | A23b | + | − | 16.7 | — |
| | A23b amphoteric | − | + | 19.6 | — |
| | A23b | + | + | 16.1 | — |
| 13 | A12 | − | − | 24.9 | — |
| | A12 | + | − | 21.6 | c |
| | A12 anionic | − | + | 18.8 | — |
| | A12 | + | + | 16.1 | c |
| 14 | A1 | − | − | 28.9 | — |
| | A1 | + | − | 21.4 | b |
| | A1 anionic | − | + | 21.4 | — |
| | A1 | + | + | 17.1 | — |
| 15 | A8 | − | − | 29.6 | — |
| | A8 | + | − | 23.4 | b |
| | A8 anionic | − | + | 19.7 | — |
| | A8 | + | + | 15.6 | — |
| 16 | A13 | − | − | 19.6 | — |
| | A13 anionic | + | − | 15.8 | — |

[1] 6% dilution in distilled water; corresponds to 0.1% R$_f$-surfactant and 0.02% R$_f$-synergist
[2] Ingredient present (+), absent (−)
[3] Clarity: — = clear; a = opalescent; b = slight precipitate; c = precipitate
[4] Deriphat 160C, General Mills, Inc.

EXAMPLES 18 TO 25

Table 4 shows that R$_f$-synergists of widely diverse types will all effectively depress the surface tension of a typical R$_f$-surfactant from its initial surface tension of 28.9 dynes/cm (see Table 3).

Surface tensions of 15–17 dynes/cm are generally attainable, a remarkable depression of 11–13 dynes/cm. Even in the absence of magnesium salt, substantial synergistic effects are observed. With rare exception, surface tension values as low as 15–16 dynes/cm at such low fluorinated surfactant concentration have not previously been reported. In fact, these low synergistic surface tensions approach 14.5-15.0 dynes/cm, which is believed to be the lowest theoretically attainable value for an aqueous fluorosurfactant.

EXAMPLES 32 TO 39

Table 6 shows how the CMC plots of the subject compositions are effected by the addition of a preferred Table 4

| Effect of $R_f$-Synergist Types | | | |
|---|---|---|---|
| Anionic $R_f$-Surfactant | A1 | | 1.67%[1] |
| $R_f$-Synergist | Variable | | |
| Solvent | E4 | | 25% |
| Magnesium Sulfate Heptahydrate | | | 0.5% |

| Example Number | $R_f$-Synergist | Concentrate % | $MgSO_4 \cdot 7 H_2O$[2] | Surface Tension[3] | Clarity[4] |
|---|---|---|---|---|---|
| 18 | B6 | 0.33 | − | 21.4 | b |
|    |    |      | + | 17.1 | b |
| 19 | B9 | 0.33 | − | 18.8 | b |
|    |    |      | + | 17.5 | — |
|    |    | 1.10 | − | 18.3 | — |
|    |    |      | + | 15.0 | — |
| 20 | B12 | 0.33 | − | 21.1 | — |
|    |     |      | + | 17.6 | b |
|    |     | 1.10 | − | 23.3 | b |
|    |     |      | + | 15.8 | — |
| 21 | B14 | 0.33 | − | 21.9 | — |
|    |     |      | + | 18.3 | b |
|    |     | 1.10 | − | 19.4 | b |
|    |     |      | + | 16.8 | — |
| 22 | B18 | 0.33 | − | 20.1 | — |
|    |     |      | + | 16.6 | — |
| 23 | B19 | 0.33 | − | 19.4 | — |
|    |     |      | + | 18.8 | — |
| 24 | B17 | 0.33 | + | 18.2 | b |
| 25 | B21 | 0.33 | − | 18.5 | — |
|    |     |      | + | 16.2 | — |

[1]Ingredients corrected for dilution as necessary; 100% actives
[2]Ingredient present (+), absent (−)
[3]6% dilution in distilled water corresponds to 0.10% $R_f$-surfactant, and 0.02% $R_s$-synergist for 0.33% $R_f$-synergist; 0.067% $R_f$-synergist for 1.1% $R_f$-synergist
[4]Clarity: — = clear, b = slight precipitate

EXAMPLES 26 TO 31

Table 5 shows how in examples 27 and 28 versus 26 and examples 30 and 31 versus 29, compositions with $R_f$-synergist exhibit much lower surface tensions then do the $R_f$-surfactants alone, and certain $R_f$-surfactant/$R_f$-synergist mixtures are better than others. The marked improvement in properties is apparent even at 0.01% concentration and a divalent salt is not present.

$R_f$-synergist. The surface tensions are progressively improved over the entire concentration range as $R_f$-synergist B6 is added, both with and without magnesium ions present. Values with magnesium are considerably better and the solutions are apparently more stable. Approximately 10% of the synergist is sufficient to attain a minimum surface tension.

Table 5

| | Surface Tension Versus Concentration | | | | | | | |
|---|---|---|---|---|---|---|---|---|
| Example Number | Solids Composition[1] | | | | Surface Tension (dynes/cm) % Solids | | | |
| | $R_f$-Surfactant | Parts | $R_f$-Synergist | Parts | 1.0 | .1 | .01 | .001 | .0001 |
| 26 | A1 | 100 | — | — | — | 27 | 30 | 42 | 57 |
| 27 | A1 | 75 | B1 | 25 | — | 16.7 | 19.8 | 33.8 | 51.5 |
| 28 | A2 | 82 | B2 | 18 | — | 16.3 | 22.1 | 32.9 | 54.3 |
| 29 | A23a | 100 | — | — | 20 | 20 | 21 | 28 | 61 |
| 30 | A23b | 72 | B1 | 25 | — | 15.1 | 15.6 | 27.3 | 54.2 |
| 31 | A23c | 82 | B2 | 18 | — | 16.0 | 16.7 | 34.0 | 60.5 |

[1]The compositions contain 45% solids in 20/80 hexylene glycol/water

Table 6

| | Surface Tension Versus Concentration | | | | | |
|---|---|---|---|---|---|---|
| | Solids Composition[1] | | | Surface Tension- (dynes/cm) | | |
| Example Number | $R_f$-Surfactant A3 parts | $R_f$-Synergist B6 parts | $MgSO_4 \cdot 7H_2O$ parts | % Solids[2,3] | | |
| | | | | .1 | .01 | .001 |
| 32 | 100 | — | — | 28.2 | 26.6 | 48.1 |
| 33 | 100 | 6.6 | — | 21.7 | 20.2 | 41.7 |
| 34 | 100 | 13.2 | — | 18.9[b] | 21.4 | 42.1 |
| 35 | 100 | 20.0 | — | 19.0[b] | 20.6 | 40.0 |
| 36 | 100 | — | 30 | 19.7 | 20.1 | 43.9 |
| 37 | 100 | 6.6 | 30 | 17.3 | 16.5 | 34.7 |
| 38 | 100 | 13.2 | 30 | 16.4 | 15.7 | 30.8 |
| 39 | 100 | 20.0 | 30 | 15.8 | 15.8 | 30.0 |

[1]The compositions contain approximately 2% solids in 25/75 butyl carbitol/water
[2]Based on $R_f$-Surfactant A3
[3]Clarity: clear unless denoted b, slight precipitate with 1 day

EXAMPLES 40 TO 67

Table 7 shows Examples 40 to 67 can be prepared as compositions which exhibit improved surface properties in the context of this patent.

Table 7

Other Effective Fluorinated Synergist/Surfactant Compositions

| Example Number | $R_f$-Surfactant | $R_f$-Synergist | Example Number | $R_f$-Surfactant | $R_f$-Synergist |
|---|---|---|---|---|---|
| 40 | A4 | B3 | 54 | A26 | B20 |
| 41 | A5 | B4 | 55 | A27 | B1 |
| 42 | A6 | B5 | 56 | A28 | B15 |
| 43 | A7 | B7 | 57 | A29 | B16 |
| 44 | A9 | B8 | 58 | A31 | B1 |
| 45 | A10 | B10 | 59 | A32 | B1 |
| 46 | A11 | B11 | 60 | A33 | B |
| 47 | A19 | B13 | 61 | A34 | B1 |
| 48 | A20 | B6 | 62 | A35 | B1 |
| 49 | A21 | B6 | 63 | A36 | B1 |
| 50 | A22 | B17 | 64 | A37 | B1 |
| 51 | A24 | B19 | 65 | A38 | B1 |
| 52 | A25 | B20 | 66 | A39 | B1 |
| 53 | A26 | B21 | 67 | A43 | B1 |

What is claimed is:

1. A method of improving the surface tension property of cationic, anionic, non-ionic, amphoteric or mixed function fluorinated surfactant by employing in conjunction with said surfactants an effective amount, to increase the surface tension reducing property of said surfactant, of a fluorinated synergist of the formula $$(R_f)_n T_m Z$$

wherein
$R_f$ is a straight or branched chain perfluoroalkyl of 1 to 18 carbon atoms or said perfluoroalkyl substituted by perfluoroalkoxy of 2 to 6 carbon atoms,
$n$ is an integer of 1 or 2,
T is a divalent group —$R_3$— or a group —$R_3$—$SCH_2CHR_1$— wherein $R_3$ is straight or branched chain alkylene or haloalkylene of 1 to 12 carbons, arylene of 6 to 12 carbons, alkylenethioalkylene or alkyleneiminoalkylene of 2 to 12 carbons where in said imino group the nitrogen is secondary or tertiary and $R_1$ is hydrogen or alkyl of 1 to 12 carbons,
Z is a polar group selected from —$CONR_1R_2$, —CN, —$CONR_1COR_2$, —$SO_2NR_1R_2$, —$R_3(O_2CR_1)$ and —$CO_2R_1$ where $R_1$ and $R_2$ are independently hydrogen, alkyl of 1 to 12 carbons or alkyl of 1 to 12 carbons substituted with 1 or more —OH, —$COCH_3$, —SH, —$CONH(CH_3)$, and $R_3$ is as defined above, with the proviso that said synergist is neutral,
$m$ is an integer from 0 to 2, and said fluorinated synergist having a solubility in water at 25° C. below 0.01% by weight.

2. A method of claim 1 wherein said fluorinated surfactant is of the formula $$(R_f)_n A_m Q$$

wherein
$R_f$, $n$ and $m$ are as defined above,
Q is a water solubilizing group which is an anionic, cationic, non-ionic or amphoteric moiety or a combination of such moieties,
A is a multivalent linking group, preferably alkylene of 1 to 12 carbon atoms; phenylene; alkyl substituted phenylene; or the group $C_6H_5YC_6H_5$ where Y is alkylene of carbon atoms, oxygen or sulfur; sulfonamidoalkylene; or carbonamidoalkylene.

3. A method of claim 1 wherein the $R_f$ groups in both the synergist and the surfactants are perfluoralkyl of 5 to 12 carbon atoms.

4. The method according to claim 1, wherein said fluorinated surfactant in conjunction with said fluorinated synergist exhibits an aqueous solubility of at least 0.1% by weight.

5. A surfactant composition having improved surface tension properties containing a mixture of cationic, anionic, non-ionic, amphoteric or mixed function fluorinated surfactant and an effective amount to increase the surface tension reducing property of said surfactant, of a fluorinated synergist of the formula $$(R_f)_n T_m Z$$

wherein
$R_f$ is a straight or branched chain perfluoroalkyl of 1 to 18 carbon atoms or said perfluoroalkyl substituted by perfluoroalkoxy of 2 to 6 carbon atoms,
$n$ is an integer of 1 or 2,
T is a divalent group —$R_3$— or a group —$R_3$—$SCH_2CHR_1$— wherein $R_3$ is straight or branched chain alkylene or haloalkylene of 1 to 12 carbons, arylene of 6 to 12 carbons, alkylenethioalkylene or alkyleneiminoalkylene of 2 to 12 carbons where in said imino group the nitrogen is secondary or tertiary and $R_1$ is hydrogen or alkyl of 1 to 12 carbons,
Z is a polar group selected from —$CONR_1R_2$, —CN, —$CONR_1COR_2$, —$SO_2NR_1R_2$, —$R_3(O_2CR_1)$ and —$CO_2R_1$ where $R_1$ and $R_2$ are independently hydrogen, alkyl of 1 to 12 carbons or alkyl of 1 to 12 carbons substituted with 1 or more —OH, —$COCH_3$, —SH, —$CONH(CH_3)$, and $R_3$ is as defined above, with the proviso that said synergist is neutral,
$m$ is an integer from 0 to 2, and said fluorinated synergist having a solubility in water at 25° C. below 0.01% by weight.

6. A surfactant composition according to claim 5, wherein said fluorinated surfactant is of the formula $$(R_f)_n A_m Q$$

wherein
$R_f$, $n$ and $m$ are as defined above,
Q is a water solubilizing group which is an anionic, cationic, non-ionic or amphoteric moiety or a combination of such moieties, A is alkylene of 1 to 12 carbon atoms; phenylene; alkyl substituted phenylene; or the group $C_6H_5YC_6H_5$ where Y is alkylene of 1 to 4 carbon atoms, oxygen or sulfur; sulfonaminoalkylene; or carbonamidoalkylene.

7. The surfactant composition according to claim 6, wherein the $R_f$ groups in both the synergistic and the surfactants are perfluoroalkyl of 5 to 12 carbon atoms.

8. The surfactant composition according to claim 5, wherein fluorinated surfactant-fluorinated synergistic composition exhibits an aqueous solubility of at least 0.1% by weight.

* * * * *